US006994722B2

(12) United States Patent
DiCarlo (10) Patent No.: US 6,994,722 B2
(45) Date of Patent: Feb. 7, 2006

(54) IMPLANT HAVING IMPROVED FIXATION TO A BODY LUMEN AND METHOD FOR IMPLANTING THE SAME

(75) Inventor: Paul DiCarlo, Middleboro, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 494 days.

(21) Appl. No.: 09/898,936

(22) Filed: Jul. 3, 2001

(65) Prior Publication Data

US 2003/0009211 A1   Jan. 9, 2003

(51) Int. Cl.
A61F 2/06 (2006.01)
(52) U.S. Cl. .................. 623/1.13; 623/1.36; 623/1.38; 623/1.11
(58) Field of Classification Search .............. 623/1.1, 623/1.12, 1.36, 1.13, 1.38, 1.39, 11, 66
See application file for complete search history.

(56) References Cited

U.S. PATENT DOCUMENTS

| | | | |
|---|---|---|---|
| 3,726,279 A * | 4/1973 | Barefoot et al. ............ 606/151 |
| 4,652,264 A | 3/1987 | Dumican |
| 4,728,328 A * | 3/1988 | Hughes et al. ........... 623/23.69 |
| 4,740,207 A | 4/1988 | Kreamer |
| 5,061,274 A | 10/1991 | Kensey |
| 5,324,775 A | 6/1994 | Rhee et al. |
| 5,344,444 A | 9/1994 | Glastra |
| 5,415,619 A | 5/1995 | Lee et al. |
| 5,522,881 A * | 6/1996 | Lentz ........................ 623/1.13 |
| 5,617,878 A | 4/1997 | Taheri |
| 5,718,717 A | 2/1998 | Bonutti |
| 5,769,882 A | 6/1998 | Fogarty et al. |
| 5,769,884 A * | 6/1998 | Solovay ..................... 623/1.13 |
| 5,824,036 A * | 10/1998 | Lauterjung ................. 623/1.11 |
| 5,855,598 A | 1/1999 | Pinchuk |
| 5,865,814 A | 2/1999 | Tuch |
| 5,964,744 A * | 10/1999 | Balbierz et al. ............ 604/530 |
| 6,013,100 A * | 1/2000 | Inoue ........................ 623/1.13 |

(Continued)

FOREIGN PATENT DOCUMENTS

EP   0 689 806   1/1996

(Continued)

OTHER PUBLICATIONS

John J. Castronuovo, Jr., M.D.; Kevin V. James, M.D.; Michael Resnikoff, M.D.; Edward R. McLean, M.D.; and John K. Edoga, M.D., "Laparoscopic-assisted abdominal aortic aneurysmectomy," *Journal of Vascular Surgery*, vol. 32, No. 2, Aug. 2000, pp. 224-233.

(Continued)

Primary Examiner—Corrine McDermott
Assistant Examiner—Christopher Prone
(74) Attorney, Agent, or Firm—RatnerPrestia (57) ABSTRACT

A device for improving fixation and sealing of a prosthetic component when implanted in a body lumen during laparoscopic, endovascular, or open surgical procedures. In one embodiment, the prosthetic component comprises a graft having a hem defining an interior space. Enclosed within the space is an absorbent cord. The cord expands as it comes in contact with body fluids. The expansion due to the absorbed fluids forms a seal closely following the irregular shape of the lumen and improves fixation at the junction of the body lumen and the prosthetic component. Hem and cord arrangement also used to improve fixation of one prosthetic component to another in a modular graft. In another embodiment, an attachment tab has one part affixed to the outer periphery of the graft and another part attached to an area adjacent to the body lumen upon implantation, to resist forces tending to move the implant.

36 Claims, 10 Drawing Sheets

U.S. PATENT DOCUMENTS

| | | | |
|---|---|---|---|
| 6,048,966 A | | 4/2000 | Edwardson et al. |
| 6,059,823 A | * | 5/2000 | Holman et al. ............ 623/1.15 |
| 6,083,522 A | | 7/2000 | Chu et al. |
| 6,147,168 A | | 11/2000 | Jamiolkowski et al. |
| 6,159,240 A | * | 12/2000 | Sparer et al. .............. 623/2.36 |
| 6,172,219 B1 | | 1/2001 | Callegaro et al. |
| 6,177,095 B1 | | 1/2001 | Sawhney et al. |
| 6,371,982 B2 | * | 4/2002 | Berg et al. ................... 623/1.4 |
| 6,395,019 B2 | * | 5/2002 | Chobotov ................. 623/1.13 |

FOREIGN PATENT DOCUMENTS

EP        0 723 766        7/1996

OTHER PUBLICATIONS

Denton A. Cooley, M.D., "Surgical Treatment of Aortic Aneurysms," W.B. Saunders Company, 1986, pp. 114-121.

Darwin Eton, M.D., FACS; Thomas T. Terramani, M.D.; and Michael Katz, M.D., "Staged Thoracic and Abdominal Aortic Aneurysm Repair Using Stent Graft Technology and Surgery in a Patient with Acute Renal Failure," *Annals of Vascular Surgery*, vol. 14, No. 2, 2000, pp. 114-117.

* cited by examiner

IMPLANT HAVING IMPROVED FIXATION TO A BODY LUMEN AND METHOD FOR IMPLANTING THE SAME

FIELD OF THE INVENTION

The present invention relates to surgical implants and more particularly to the improvement of fixation and sealing of a prosthetic component to a body lumen.

BACKGROUND OF THE INVENTION

In surgical procedures for treating aneurysms and other problems in the vasculature, it has been common practice to employ surgical implants, such as endovascular implants. Such devices face many fixation challenges caused primarily by anatomical changes that occur as the disease advances and by the irregular shape of the body lumen where the devices are deployed. To combat this issue, many types and shapes of stents are placed inside a graft material to fixate the graft into place. This technique, however, has certain limitations. For example, in repairing abdominal aortic aneurysms using this technique, there must exist a minimum distance of one centimeter from the renal arteries to the aneurysm. In addition, the radially expanded cross-sectional shape of most stents is circular, while the cross-sectional shape of the body lumen where it is being placed is non-circular.

Standard use of grafts during laparoscopic and open surgical procedures rely on suturing the internal circumference of the artery to the circumference of the graft which results in a stressful and time-consuming operation for a patient and medical professional.

SUMMARY OF THE INVENTION

The present invention provides a device that can be implanted in a body lumen for the purpose of reconstructing or making a repair of the lumen. In a first embodiment of the invention, the device includes a prosthetic component having a graft with a hem formed thereon. The hem defines an interior space within itself that is used to contain a cord. The cord is constructed to contain an absorbent material that expands upon contact with a fluid, such as blood. The expansion of the cord caused by the absorption of the fluid aids in fixating the graft about an irregularly shaped body lumen such as an aorta. The expanding cord helps to fixate the prosthetic component to the body lumen, oppose the downward force of the blood flow on the device, and form a better seal to reduce endoleaks at the junction of the graft and the body lumen. A method for implanting a device in a body lumen according to this embodiment includes introducing the device into the body lumen and contacting the cord with fluid to aid in fixating the prosthetic component against the body lumen.

In another exemplary embodiment of the device, a first and a second prosthetic component are joined together and their junction exhibits improved fixation because of the use of an expandable cord which is part of the inserted prosthetic component. The second prosthetic component having a hem containing the expandable cord is adapted to fit into the first prosthetic component so that the hem contacts the interior wall of the first prosthetic component. As fluid is absorbed by the expandable cord its expansion will cause it to come in close contact with all irregular protrusions and depressions on the interior wall and will form a good seal and improve fixation between the first and second prosthetic component. The expandable cord within the second prosthetic component is used to fixate the two prosthetic components to each other. The expansion of the cord improves the fixating by opposing forces that tend to separate the prosthetic components.

According to another embodiment of the invention, one or more attachment tabs are attached to the outer periphery of the prosthetic component. Each tab may be configured as a flap unsupported at one end, such as its distal end. The tabs are attached at their other end, typically their proximal end, to the outer periphery of the graft and extend radially outward from this attachment point to the graft. When the prosthetic component is deployed, a part of each tab other than the attached end, such as the unattached end, is attached to an adjacent area of the body surrounding the lumen. The tabs are provided as fixation devices for the prosthetic component and assist in reducing downward movement by sharing the load of the implant over the length of the prosthetic component. A method for implanting a device according to this embodiment involves introducing the device in a body lumen and attaching the second part of the attachment tab to an adjacent area of the body surrounding the prosthetic component. These tabs may be used alone or in combination with the features described in connection with the first embodiment of the present invention.

A better understanding of these and other aspects of the invention will hereinafter more fully appear, and will be more particularly pointed out in the appended claims. Reference is now made to the following detail description taken in conjunction with the accompanying drawings. BRIEF

DESCRIPTION OF THE DRAWINGS

The invention will hereinafter become more fully apparent from the following description of the annexed drawings wherein:

FIG. 5a is a perspective view illustrating a tab extension ring of still another embodiment of the invention;

FIG. 5b is a plan view of the tab extension ring shown in FIG. 5a;

DESCRIPTION OF THE PREFERRED EMBODIMENTS

Figure 1:
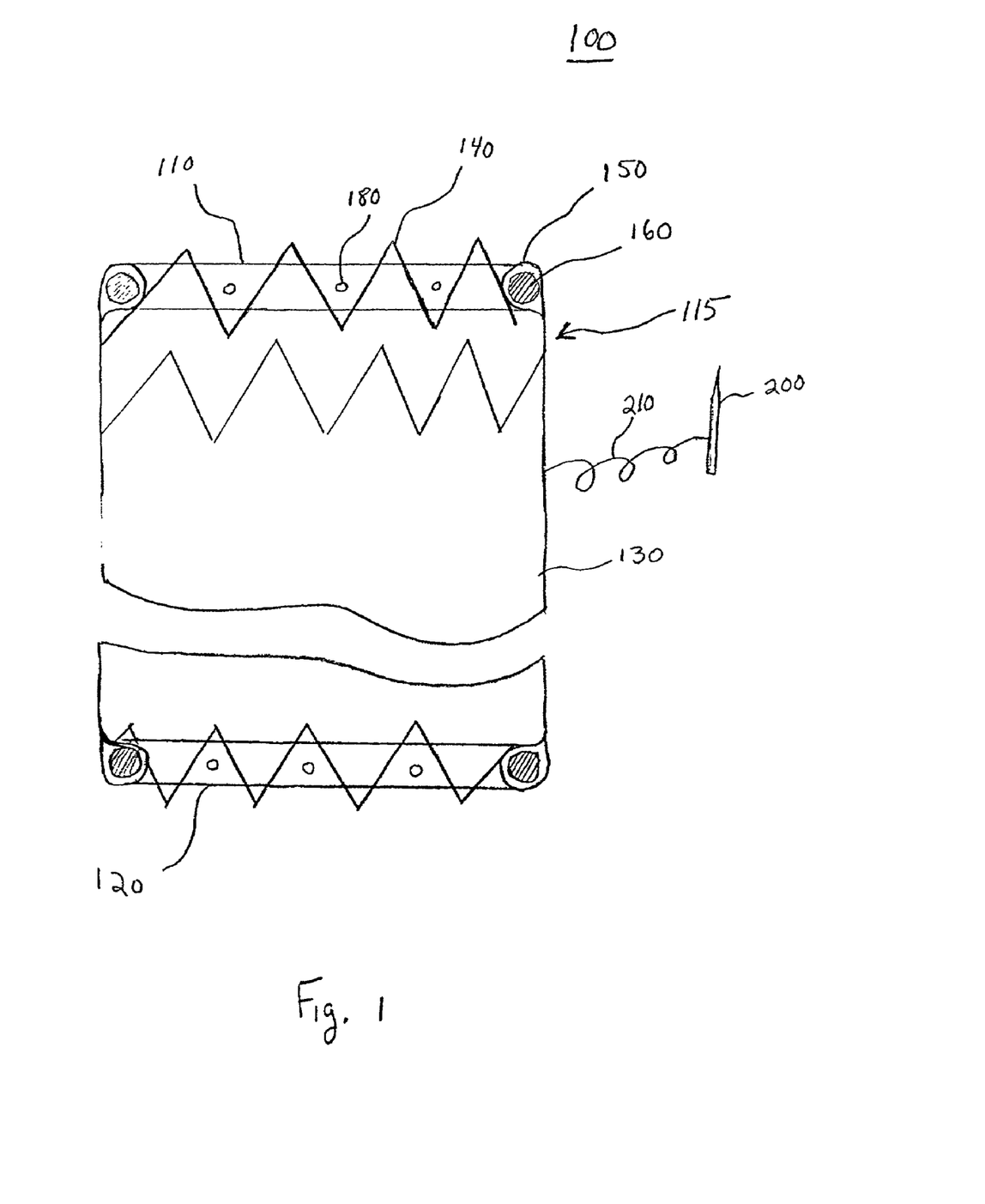
FIG. 1 shows a plan view partly in section of an embodiment of the invention.

Referring now to FIG. 1, there is shown an endovascular implant or device 100. The device 100 comprises a prosthetic component 115 which includes a graft 130 and may also include a stent 140 positioned within the inside circumference of the graft 130. When the device is deployed endovascularly, it is desirable that the prosthetic component includes a stent. On the other hand, the prosthetic component 115 may consist solely of a graft, which may be desirable when the device is deployed laparoscopically or during open surgical procedures. Graft 130 is comprised of a woven fabric such as Dacron, polyester, or polytetrafluoroethylene, to form a cylindrical wall surrounding stent 140. Stent 140 is a wire mesh and can be of any suitable type and configuration as are well known in the art. For example, stent 140 may be braided, or filamentary, or laser cut, or etched and may be self-expandable or balloon-expandable. One exemplary form of a self-expanding stent is made from a shape-memory alloy of nickel and titanium.

FIG. 1 shows a first hem 110 at a distal end of prosthetic component 115 and also illustrates another embodiment of the invention by the inclusion of a second hem 120 at a proximal end of the prosthetic component 115. As used herein, the term "proximal" shall mean a location closer to an access point from outside the body and the term "distal" shall mean a location farther away from the access point, which is typically in the leg of a patient. The first hem 110 and the second hem 120 are similarly constructed as described herein below using the first hem 110 as an example.

Figure 6:
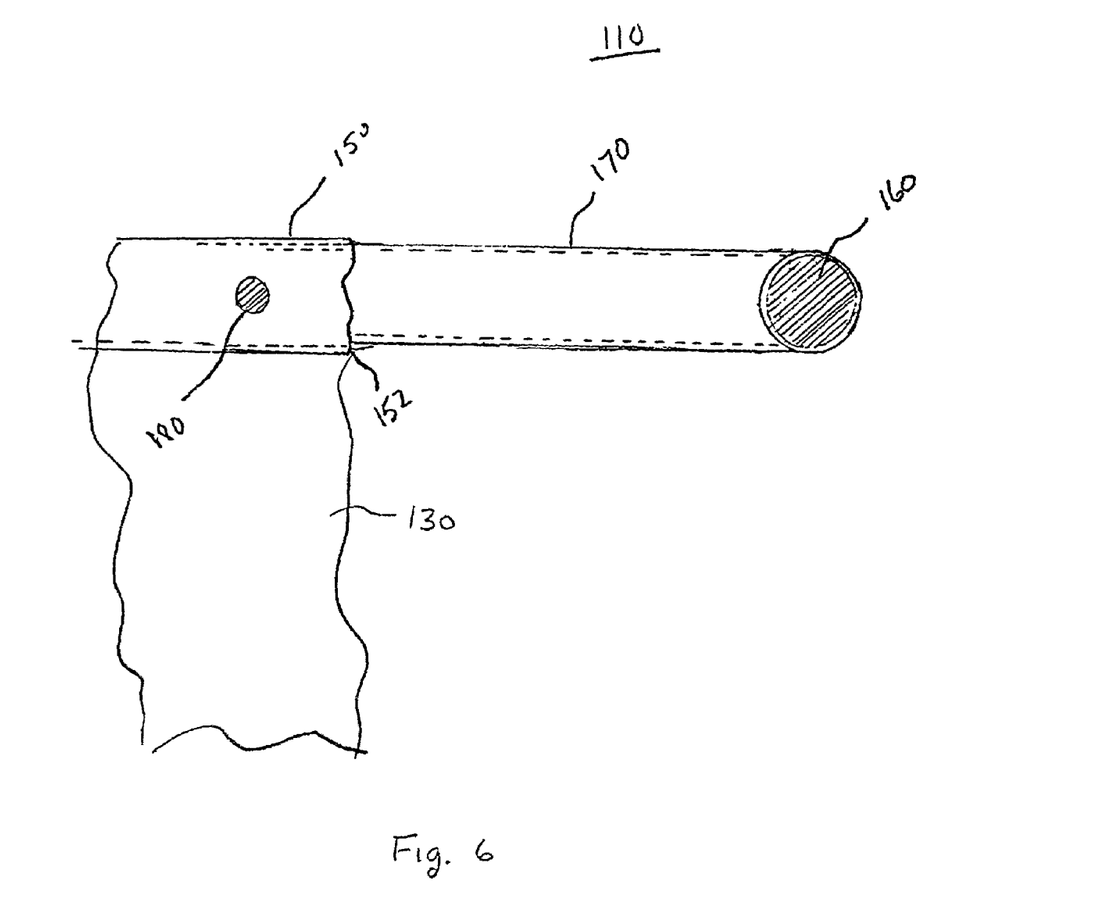
FIG. 6 is a cut-away perspective view of one of the hems shown in FIG. 1.

Referring to FIG. 6, the graft 130 has a first hem 110 forming a casing 150 which defines an interior space 152 therein. Enclosed by the casing 150 and within the interior space 152 is an absorbent cord 160 made of a material such as Merocel® polymer or a similar absorbent material that can predictably absorb a fluid and controllably expand as a result of this absorption. As determined by medical professionals, the fluid used to first contact the absorbent cord 160 might initially be a locally administered saline solution for the purpose of establishing fixation while the flow of blood is impeded in the early stages of implant. Initially, or in the absence of pressurized fluid, the cord may only partially absorb the fluid, such as at the areas of the cord exposed to the fluid. When the flow of blood is restored, the blood itself will contact the absorbent cord 160 and will be absorbed to provide continued further fixation.

The first hem 110 has an appearance of a hem such as may be formed along or around the bottom of a skirt or at the bottom of the legs of trousers. In the case of the first hem 110, it may be constructed by folding a portion of the material of graft 130 over and onto itself and attaching it to itself to form casing 150 defining interior space 152. The hem need not necessarily be at an end of graft 130. The absorbent cord 160 is enclosed within the interior space 152 and can have any shape suitable to accommodate the particular application. More specifically, the material of cord 160, when dry, can be compressed into any regular or irregular shape as needed. Such compression might be needed to place the device in a delivery catheter. The absorbent cord 160 can have a flat ribbon shape which reduces the profile of the device. It is possible that still other shapes for cord 160 can be used. Other shapes of the cord include annular, circular, semi-circular, D-shaped, rectangular, octagonal, trapezoidal, triangular and square. The material of first hem 110 is preferably sufficiently ductile to form a suitable interior area to contain the cord and to conform to irregular shape of the body lumen. In another embodiment of the invention, first hem 110 is constructed separately without folding over the material of the graft 130. Such a separately constructed first hem 110 has a casing 150 made from a separate material other than the graft 130 and uses the separate material to form interior space 152 for containing the absorbent cord 160. The first hem 110 constructed in this manner is then attached to the graft 130 at the proper location by sewing, gluing, or weaving to the graft as a separate component.

It may be desirable to delay the time at which the fluid contacts cord 160 from the point at which fluid is permitted to contact the prosthetic component 115. For example, it may be desirable to first allow the fluid to contact stent 140 to cause the stent to radially expand (in the case when a shape memory alloy is used as the material for the stent) and then, after some time, allow cord 160 to absorb the fluid and then expand.

Referring again to FIG. 6, there is shown a perspective view of first hem 110 enlarged to better illustrate the bio-absorbable coating 170 applied to the absorbent cord 160 by unwrapping the casing 150. For the purpose of delaying fluid absorption, the absorbent cord 160 has a bio-absorbable coating 170 applied to its outer circumference which controls the rate and amount of fluid that enters into the absorbent material. As used herein, a "bio-absorbable coating" shall mean any material which can be applied as a layer over the cord and which gradually dissolves upon exposure to bodily fluid at a known rate. Polymer coating materials which can be used for the bio-absorbable coating include gelatin; polylactic acid; polyglycolic acid, polysaccharides such as celluloses, starches, dextrans, alginates and derivatives; and chlorhexidine gluconate, among others. The bio-absorbable coating thickness may be varied to regulate the amount of absorption and the type of bio-absorbable coating may be selected to absorb certain predetermined fluids, such as blood.

Figure 2:
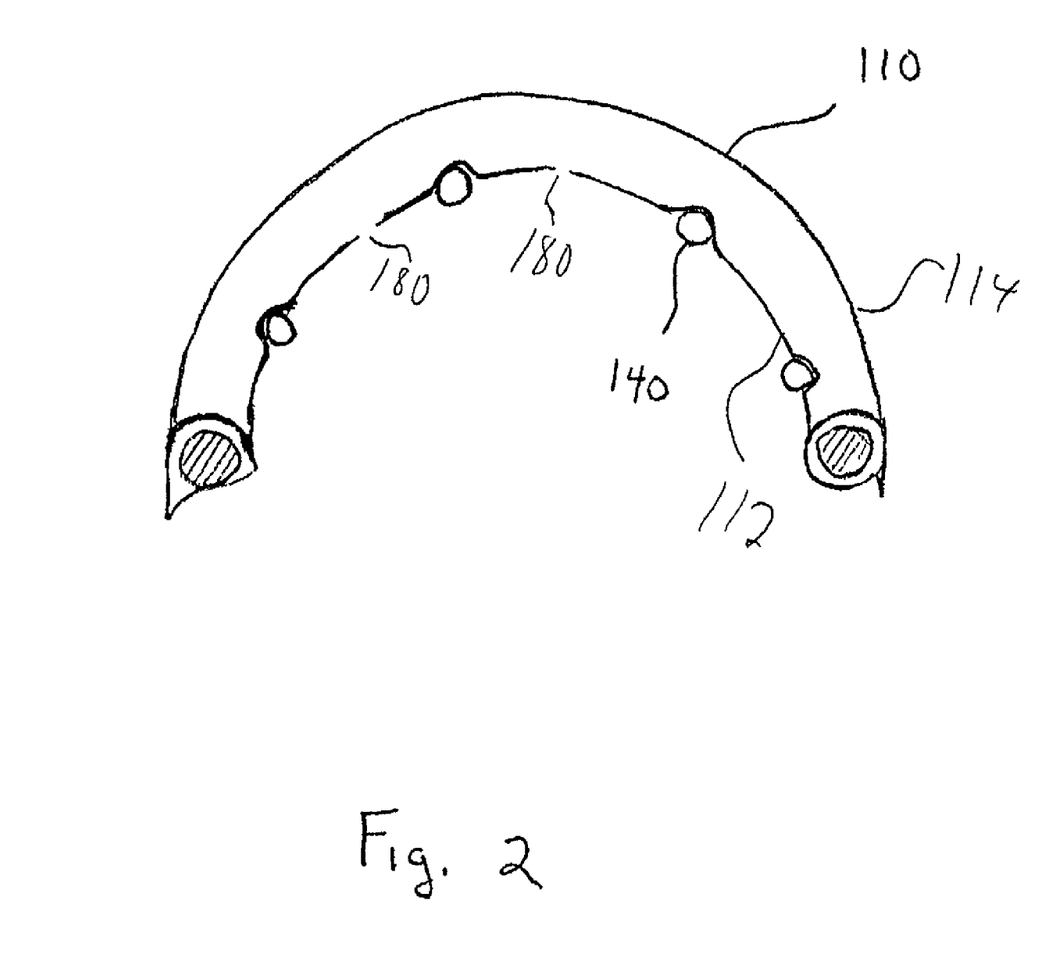
FIG. 2 illustrates a top plan view of the device of FIG. 1.

As an additional or alternative way to vary the time of fluid contact with the cord 160 and the rate of absorption by the cord 160, a plurality of holes 180 may be pierced in the casing 150 of the first hem 110 for the purpose of increasing the porosity of the first hem 110. The number of holes and the size of the holes are determined by the amount of the porosity desired. Referring to FIGS. 1 and 2, there are shown holes 180 penetrating the casing 150 from a radially inner border 112 of the casing. As yet another alternative, the material around hem 110 may have a different permeability from the remainder of the graft 130 as desired. For example, if it is desirable to shorten the time at which the fluid contacts the cord 160, it may be desirable to use a graft 130 having a first permeability at areas remote from the hem 110 and a second permeability, greater than the first permeability, at or around the hem 110. More preferably, it may be desirable for radially inner border 112 to have a relatively high permeability while radially outer border 114 has a very low permeability to minimize leakage, such as endoleaks.

Figure 3:
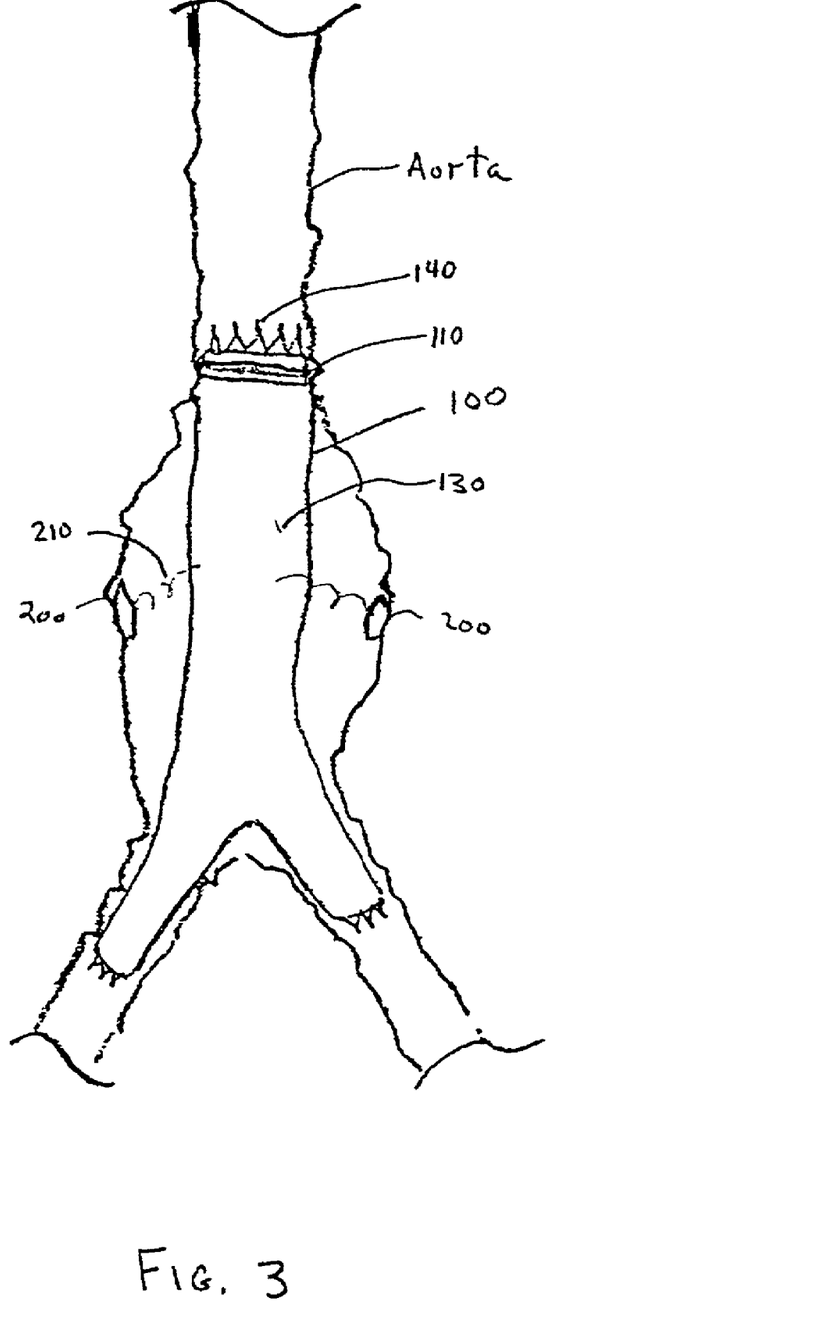
FIG. 3 is a side plan view illustrating the device of FIG. 1 in an aorta having an aneurysm.

First hem 110 is positioned and attached around the outer circumference at the distal end of prosthetic component 115. The first hem 110 is positioned so that the radial outward pressure imparted by stent 140 is equally distributed about prosthetic component 115 notwithstanding any body lumen shape irregularity encountered at the junction of the hem 110 and the inside diameter of the body lumen. As shown in FIG. 2, the stent 140 is disposed radially inside of the graft 130 and contacts inner border 112 of hem 110. FIGS. 1 and 2 illustrate the position of the first hem 110 at the distal end of prosthetic component 115. The first hem 110 is comprised of a material selected to be ductile. The ductility must be sufficient to permit the shape of first hem 110 to conform to irregular shapes of body lumens. The expansion of cord 160 and the ductility of first hem 110 allows the device 100 to conform to a human vessel wall that normally has variations and is an imperfect circle. FIG. 3 is a diagram illustrating the device 100 having its distal end, with the first hem 110, positioned within and attached to the inside circumference of a typical irregularly shaped aorta and the proximal end of device 100, without the use of the second hem 120, within irregularly shaped iliac arteries.

FIG. 1 shows the first hem 110 positioned at the distal end of the device 100 so that a portion of a the stent 140 extends beyond or distal to the most distal part of the affixed or integrally constructed first hem 110. In particular, the stent 140 is made up of a series of hoops, with each hoop being one row of the filaments comprising the stent 140. This extension promotes in-growth of tissue with the stent to improve fixation over time after implantation. FIG. 1 also shows the second hem 120 similarly positioned however at the proximal end of the device 100 so that a portion of a hoop remains extended beyond or proximal of the most proximal part of the affixed or integrally constructed second hem 120. The device 100 having the stent 140 disposed radially inside of the graft 130 with the first hem 110 formed thereon preferably has at least one hoop of the stent 140 distal relative to the first hem 110.

Figure 7:
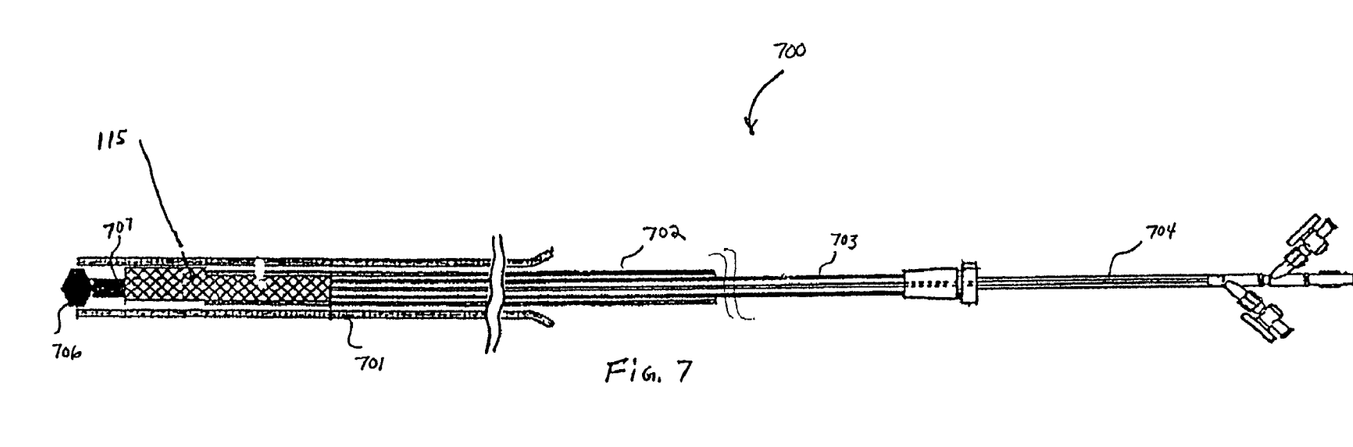
FIG. 7 is a cross-sectional side view of an introducer for use with the present invention.

Any introducer well known in the art may be used to implant endovascularly a device according this embodiment of the invention. Some typical introducers which may be used for this purpose are shown in U.S. Pat. No. 5,609,627, incorporated herein by reference. FIG. 7 is a cross-sectional view of an introducer 700 for an implant of the present invention. The prosthetic component 115 with either the first hem 110 or both the first hem 110 and the second hem 120 attached thereto as described above is configured for storage and delivery in a dry and compressed form. The first and second hems 110 and 120 in the compressed state each have a thickness of less than 30 thousandths of an inch. It is this compressed thinness that permits the use of the prosthetic component 115 with the first and second hems 110 and 120 of the invention to be delivered endovascularly through the femoral or iliac arteries.

In the embodiment shown in FIG. 7, the introducer 700 may be used to deploy a device suitable for treatment of an abdominal aorta aneurysm. Such a device could have two portions—a proximal portion for deployment in an aorta and a distal portion for deployment in an iliac artery, as is well known in the art. Introducer 700 includes outer sheath 701, which is a cylindrical tube adapted to be inserted percutaneously or by "cut-down" procedures into the vasculature from an entry point to the location within the body lumen where the prosthetic component 115 is to be implanted. Housed within outer sheath 701 is distal portion pusher 702. Distal portion pusher 702 is a cylindrical tube having an outside diameter smaller than the inside diameter of outer sheath 701. Distal portion pusher 702 is preferably slideable throughout the length of outer sheath 701. Disposed within distal portion pusher 702 is proximal portion pusher 703. Proximal portion pusher 703 is a cylindrical tube slidably contained within distal portion pusher 702. Proximal portion pusher 703 is preferably adapted to slide throughout the entire length of distal portion pusher 702. Disposed within proximal portion 703 is balloon catheter 704. Balloon catheter 704 is adapted to slide within proximal portion pusher 103. At the distal end of balloon catheter 704 is nose cone 706. Balloon 707 is attached to balloon catheter 704 between nose cone 706 and the distal end of distal portion pusher 702.

Figure 8A:
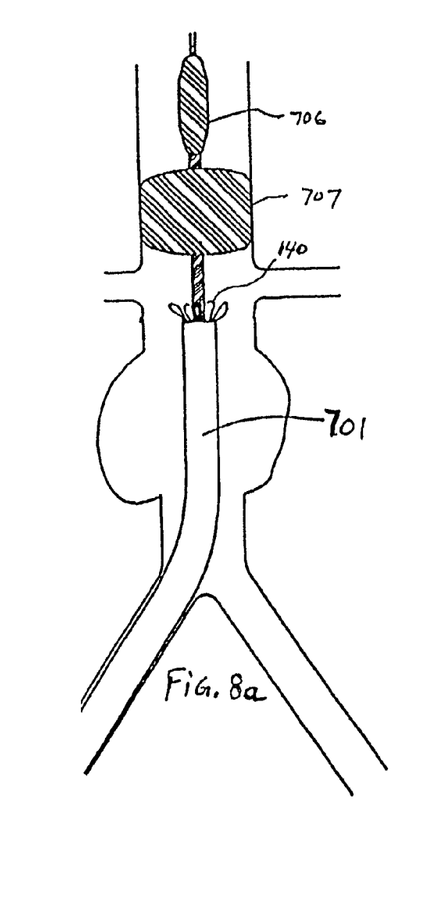
FIGS. 8a, 8b and 8c are side plan views illustrating the deployment of a device of the present invention using an introducer.
Figure 8B:
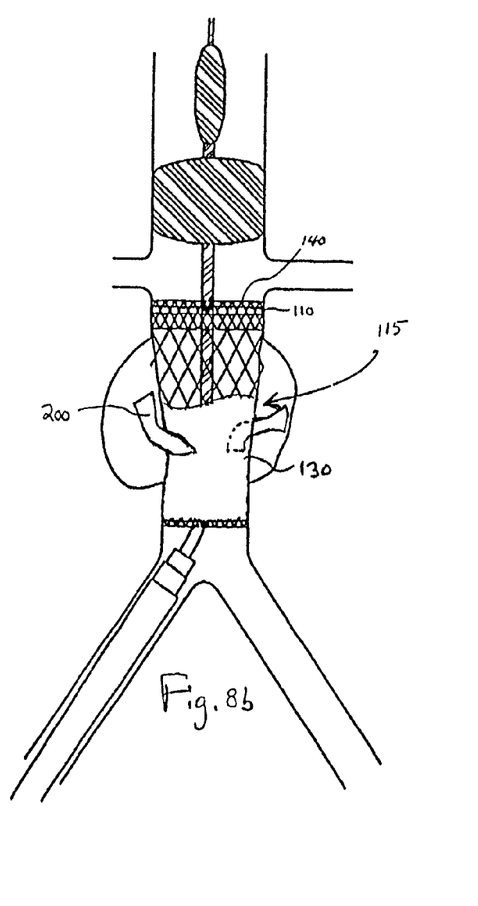
Figure 8C:
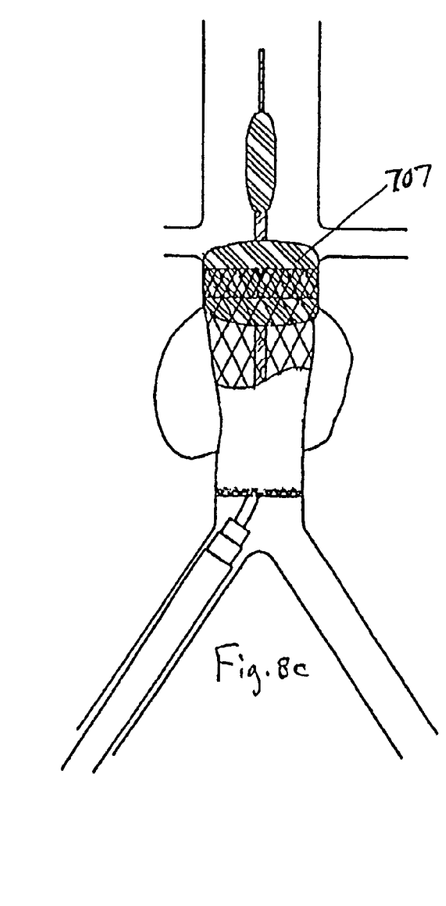

FIGS. 8a, 8b and 8c are sequential cross-sectional views of the bifurcation of the abdominal aortic artery during introduction of an implant according to the present invention. Although the introducer 700 of FIG. 7 may be used to deploy the implant shown in FIGS. 8b and 8c, it may be desirable to use an introducer with only one pusher, since the implant shown has only one portion. The prosthetic component 115 shown in FIGS. 8b and 8c are partially cut away to illustrate better the stent 140 within the graft 130 and the location of the hem 110. After compressing the device into introducer 700, the introducer is passed through an entry point (not shown). This insertion may be accomplished using well known percutaneous or cut-down techniques. Introducer 700 is then delivered to the desired delivery location within the body lumen. In the aorta, introducer 700 is positioned and balloon 707, if needed, may be inflated above the renal arteries. While maintaining distal portion pusher 702 in a fixed position, outer sheath 701 is withdrawn until prosthetic component 115 emerges from outer sheath 701 as shown in FIGS. 8a and 8b. After prosthetic component 115 is optimally aligned within the aorta, outer sheath 701 is then completely withdrawn until prosthetic component 115 is deployed into the aorta as shown in FIG. 8b. Balloon 707 is then deflated and withdrawn inside distal portion of the prosthetic component 115 where balloon 707 is re-inflated to aid in seating the prosthetic component 115, as shown in FIG. 8c.

Introducing the prosthetic component 115 into the body lumen to effectuate the implantation involves first compressing the device into an introducer 700 in a known manner. The introducer 700 is then inserted into the body lumen and positioned such that the prosthetic component 115 is at a predetermined location. It is probable that during the positioning process and even within the confines of introducer 700, cord 160 will contact body fluid. It is for that reason that an absorption impediment coating is applied to the outer surface of cord 160. Then, part of the introducer is withdrawn to cause expansion of the implant to its decompressed size. Then, the cord 160 which is by this time diminished of absorption impeding coating is made fully available by full withdrawal of the introducer to bring about a totally immersed contact with fluid to aid in fixating the prosthetic component 115 against the body lumen. This can be achieved by directing a fluid, such as pressurized saline solution, to the cord. Alternatively, this may be done by first aligning the outside circumference of the hem 110 with the inside diameter of the body lumen then removing an impediment to the flow of fluid within the body lumen to the cord 160, such as by deflating balloon 707 and allowing blood to flow and contact the cord 160.

Referring now to FIG. 1, there is also shown a second embodiment of the invention having a second hem 120 constructed of the same material and constructed in the same manner as first hem 110. It is noted however that whereas hem 110 is located and attached at the distal end of prosthetic component 115, second hem 120 is positioned and attached around the circumference of the proximal end of prosthetic component 115.

Figure 4:
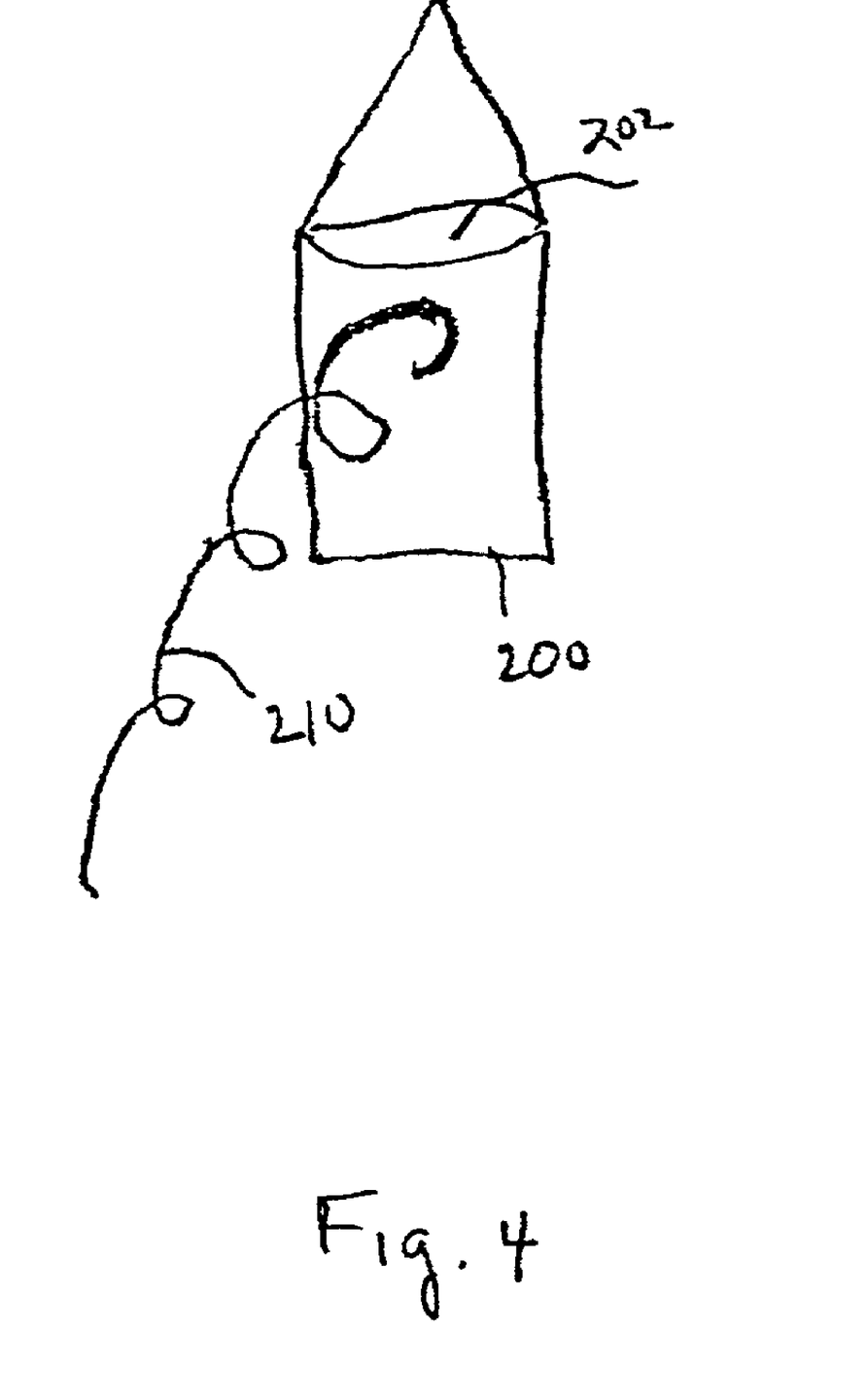
FIG. 4 shows a plan view of a tab of another embodiment of the invention.

FIG. 4 illustrates another alternative or additional embodiment for improving the fixation of a graft to a body lumen. A tab 200 comprises a shaped fabric of a material such as Dacron suitable for attachment to the graft 130 of device 100 by suture, wire, or glue. Tab 200 has a proximal end adapted for attachment to the outer periphery of the graft 130 along the length of the body of device 100. Tab 200 has a distal end that is configured to allow for attachment to areas adjacent to an implanted device 100. Tab 200 is shaped and positioned to oppose the downward force imparted by blood flow to the prosthetic component 115. This may include a wide variety of shapes such as a rectangle, square, or chevron. FIGS. 1 and 4 show an embodiment of the invention in which tab 200 is attached by a wire 210. Wire 210 may be comprised of a metal or alloy that undergoes a phase transition upon warming to body temperature, causing it to expand. A nickel and titanium alloy may be used for this purpose. Having a distal end of the wire 210 connected to the prosthetic component 115 and the proximal end connected to the tab 200, the nickel and titanium alloy wire 210 will expand at body temperature to extend the tab 200 to an area adjacent to implanted prosthetic component 115 creating a secondary fixating or stabilizing point. Typically, the prosthetic components 115 are prefabricated with tabs 200 attached at optimum locations about the outside surface. The determination of where a tab 200 should be positioned on the circumference of prosthetic component 115 may be based on pre-operation imagery of a patient. The position determination will most likely be the most advantageous for the purpose of counteracting the forces which might oppose fixation of the prosthetic component 115 and where the best fixation points are with respect to the implant of prosthetic component 115. It is also possible that placement of the tab 200 is non-critical for the situation and that randomly placed attachment tabs on the circumference is satisfactory to provide fixating and stabilizing of the prosthetic component 115.

Figures 5A, 5B:
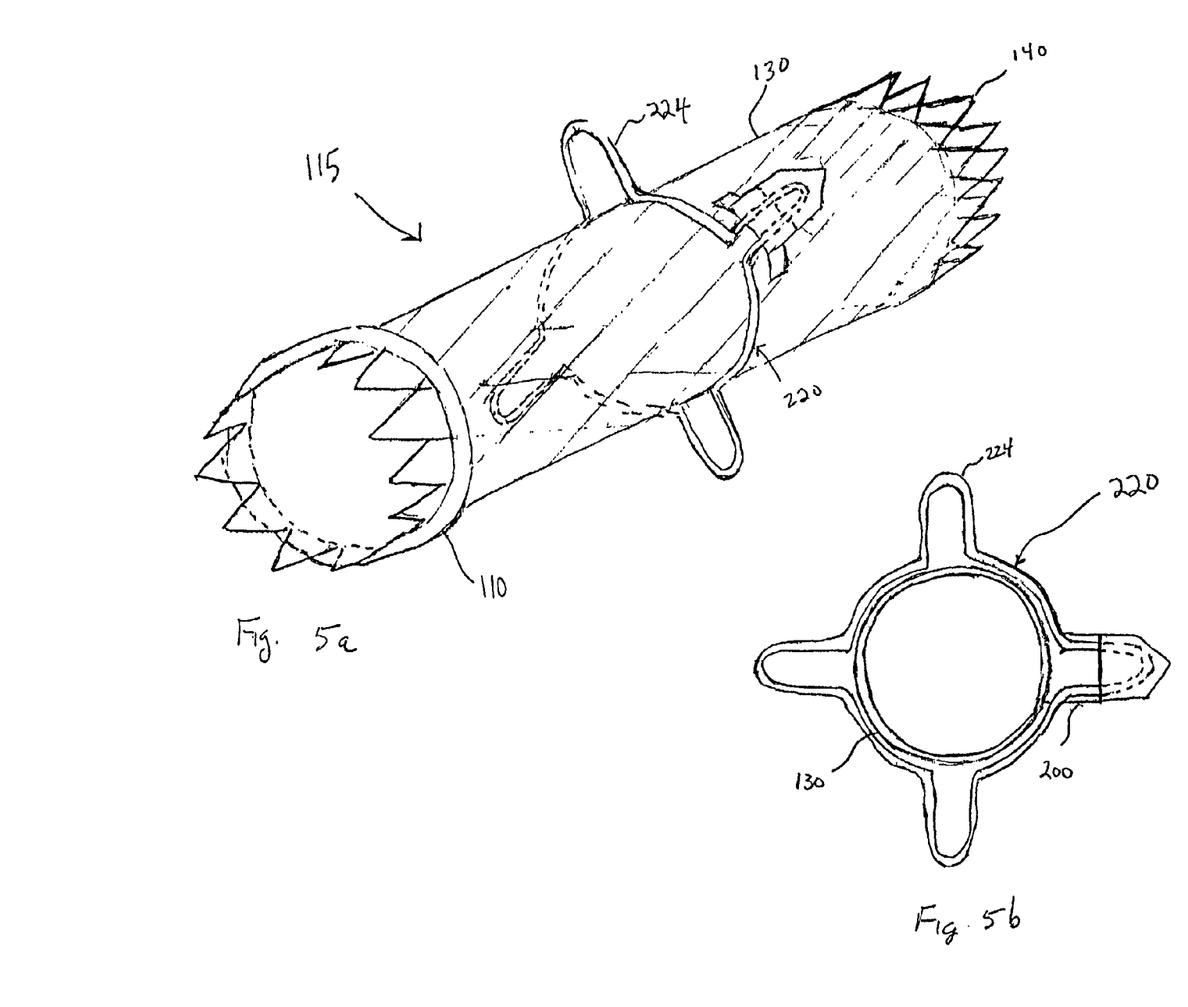

FIGS. 5a and 5b illustrate a preferred embodiment of a tab extension ring 220 which, during an open, or laparoscopic surgical procedure or mini laparotomy, can be slid along the outer periphery of the prosthetic component 115 and inserted into the tab 200, thereby rigidly extending the tabs to adjacent areas of the body for fixation of the graft. Tab extension ring 220 is constructed in the shape of a ring having spurs 224 protruding radially outward from the circumference of the ring 220. At intervals of ninety degrees around the circumference of the ring, there is an increase in the radius causing the ring diameter to increase, creating the spur 224, and then return to the original diameter. When the tab extension ring 220 is used, during an open surgical procedure, the tab 200 as shown in FIG. 4 is constructed to have a proximal end for attachment to the prosthetic component 115 and a distal end having a pouch 202 so that the spur 224 of tab extension ring 220 can slideably connect into the pouch 202.

Figure 5C:
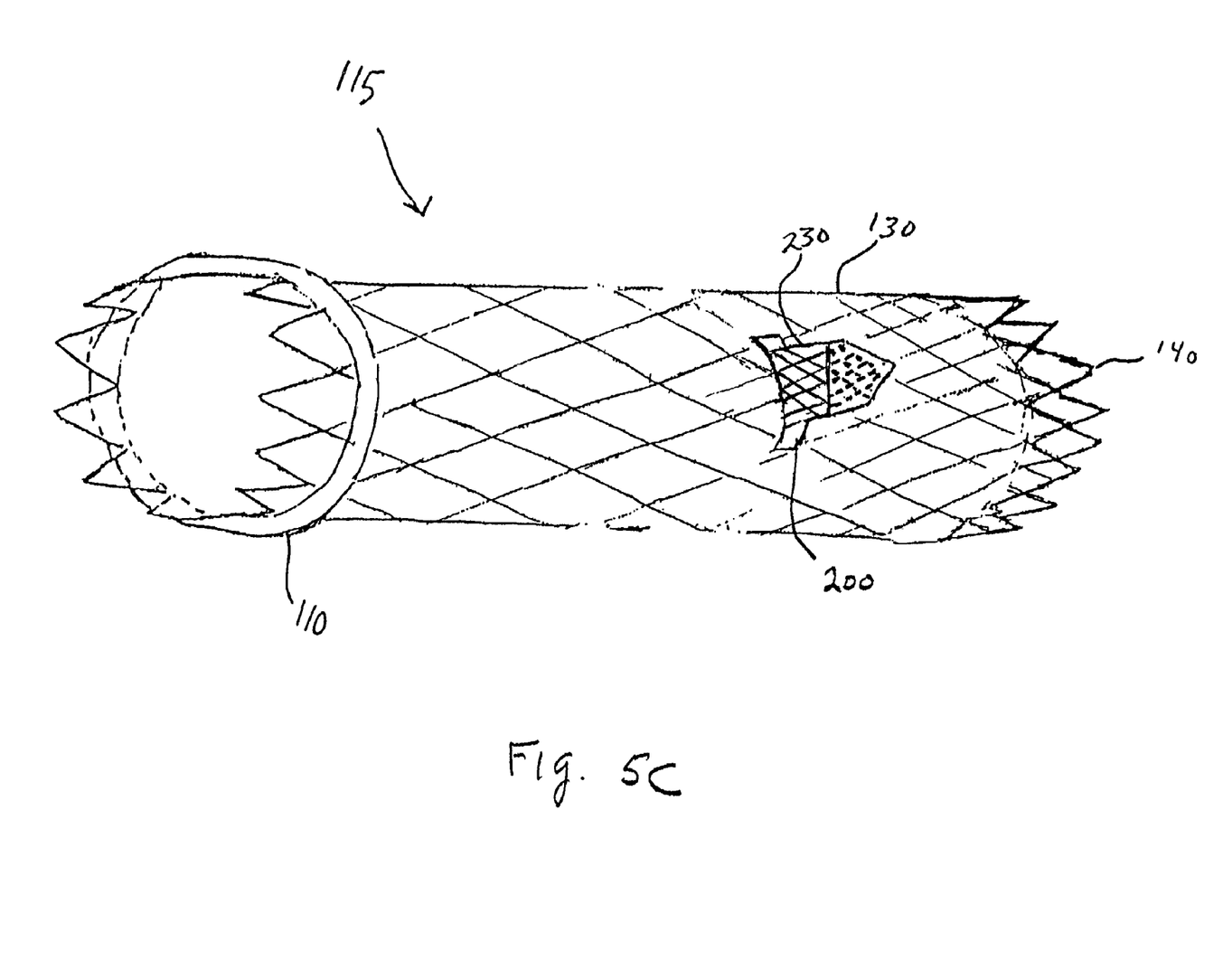
FIG. 5c is a perspective view illustrating a tab extension spur of still another embodiment of the invention.

FIGS. 5c illustrates a preferred embodiment of a tab extension spur 230 which is used during a laparoscopic or endovascular procedure. At least one tab extension spur 230 is made from the stent material, such as by weaving, and is an integral part of the stent 140. It is made to append along the outer periphery of the graft 130 and for attachment to at least one tab 200 for the purpose of radially extending the tab to contact an adjacent area of the body along the outer periphery of the prosthetic component 115. Tab extension spur 230 is pre-inserted into the at least one tab 200 prior to compression for use in the introducer. Rigid extension of the tab 200 to adjacent areas of the body for fixation of the graft occurs upon expansion of the graft after introduction at the site of use in the body lumen. Tab extension spur 230, although part of the stent 140, may be constructed by weaving in the shape of a spur, such that the spur lies adjacent the outer periphery of the prosthetic component during introduction but protrudes radially outward from the circumference of the graft 130 when decompression occurs.

A prosthetic component 115 having a graft 130 with its outer periphery having an attachment tab 200 attached to it and a second part radially outward from the graft 130 can be deployed during open surgical procedures, laparoscopically, or endovascularly. During deployment of prosthetic component 115, the tab 200 is held closely against the body of the graft within the introducer. After release from the introducer, during laparoscopic procedure or positioning during open procedure the second part of tab 200 can be attached to an adjacent area of the body surrounding the implant of the prosthetic component 115 by suturing the second part of the attachment tab to the adjacent area of the body surrounding the prosthetic component 115. If wire 210 is being used, after the wire 210 completes expansion (for example, by virtue of exposure to a fluid) then tab 200 may be sutured to the body area surrounding the implant or it may become affixed over time by tissue ingrowth. Another way during an open or laparoscopic surgical procedure only is to slide the tab extension ring 220 axially along the outer periphery of the prosthetic component 115 having the spur 224 slidably engage into the pouch 202, then suturing the radially expanded tab 200. Additionally, as shown in FIG. 8b, the prosthetic component 115 which was deployed endovascularly has tabs 200 tending to counteract against downward forces caused by the flow of blood through the implanted prosthetic component 115.

Figure 9:
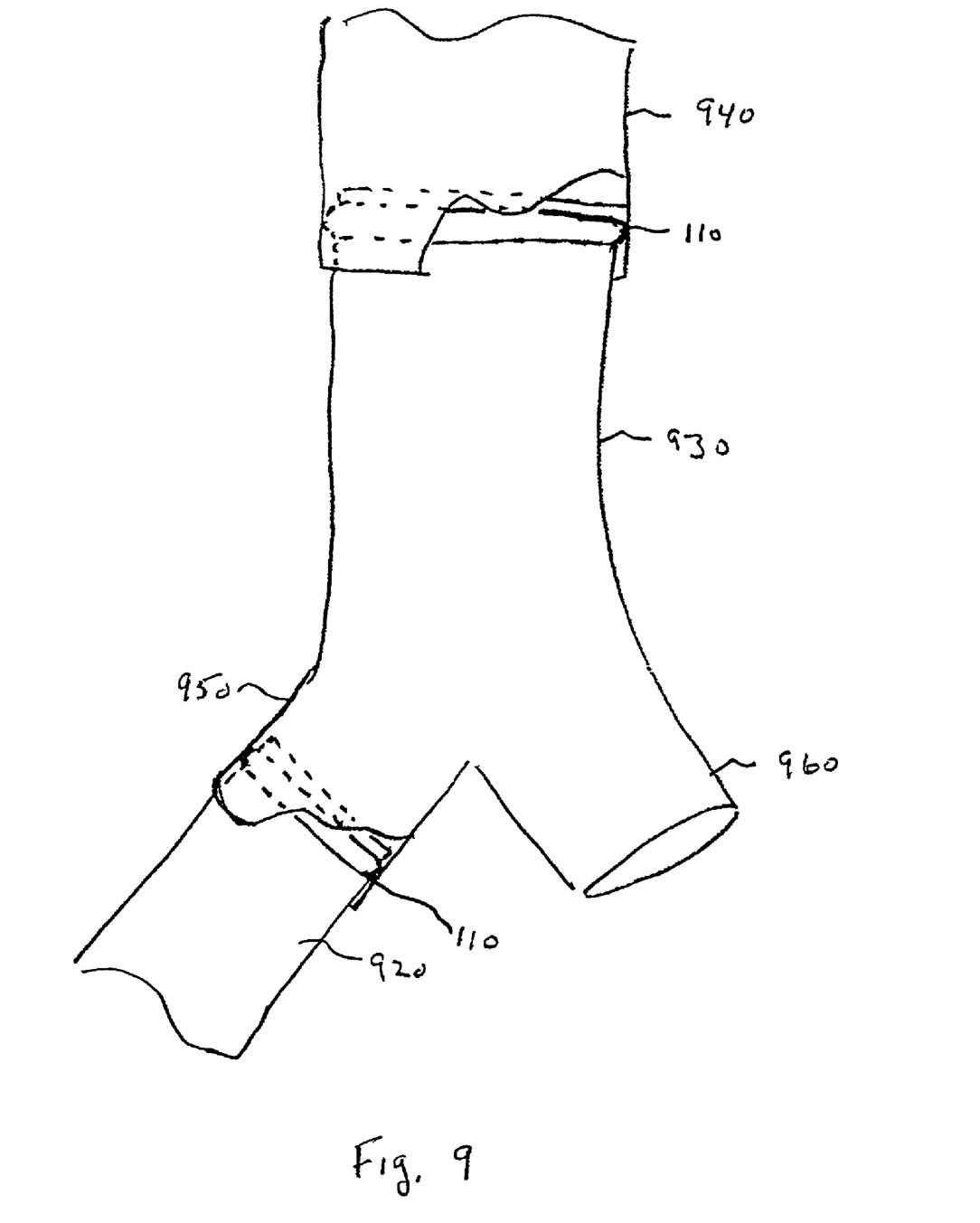
FIG. 9 shows a plan view with a cut away portion of another embodiment of the invention.

FIG. 9 illustrates another exemplary embodiment of the invention. A bifurcated prosthetic component 930, having a hem 110, containing an absorbing cord 160, is attached at a distal end to an aortic artery 940 with the bifurcated proximal ends extending into the iliac branches 950 and 960 for the common iliac arteries. In a case where it is required to implant a prosthetic component in the iliac artery, a second prosthetic component 920 is used to attach to the proximal end of the bifurcated prosthetic component 930. Second prosthetic component 920 having hem 110 is attached around the outer circumference at the distal end of prosthetic component 920. Hem 110 is positioned so that the radial outward pressure imparted by a stent or fixator improves distribution of the radial outward pressure about the periphery of prosthetic component 920 regardless of any prosthetic component 930 shape irregularities encountered at the junction of the hem 110 and the inside diameter of the prosthetic component 930. As shown in FIG. 9, the prosthetic component 920 is disposed radially inside of the iliac artery portion of prosthetic component 930 and with cord 160 expanded, due to absorption of fluid, forms a concentric circle of contact with the interior wall to seal and fixate the two prosthetic components together. Although shown as a bifurcated prosthetic component, a straight modular prosthetic component may also be used in connection with this embodiment. Also shown disposed radially about second prosthetic component 920 is a hem 110a affixed proximal to the proximal end of iliac branch 950. Hem 110a may be provided for the purpose of preventing second prosthetic component 920 from sliding distally into the iliac branch 950. More specifically, if a force is imparted to second prosthetic component 920 to cause movement of second prosthetic component 920 distally, the abutment of hem 110a against the proximal end of iliac branch 950 would stop such movement. The device of the present invention may be used in the treatment of abdominal aortic aneurysm, thoracic aortic aneurysm, occlusive disease, or SFA, among others Some of the advantages of the present invention have been disclosed that provide an absorbent cord in a hem that expands on contact with fluid to create an increased surface area for contacting the walls of a body lumen that will reduce the possibility of downward movement of the implant. The invention will allow the prosthetic component to conform to any variation in the body lumen shape and will assist in sealing the junction of the prosthetic component and the body lumen at the implant.

It should be understood, of course, that the foregoing disclosure relates to only preferred embodiments of the invention and that numerous modifications or alterations may be made therein without departing from the spirit and the scope of the invention as set forth in the appended claims.

What is claimed is:

1. A device for implantation in a body lumen comprising:
    a prosthetic component having a proximal end and a distal end and comprising a graft extending between said proximal end and said distal end and having a hem formed on said proximal end or said distal end, wherein said hem defines an interior space; and
    a cord disposed within said interior space adapted for expanding upon absorbing fluid for aiding in fixating said prosthetic component against said body lumen.

2. The device of claim 1, wherein said prosthetic component further comprises a stent disposed radially inside of said graft.

3. The device of claim 1, wherein said hem is disposed at said distal end of said prosthetic component.

4. The device of claim 3, wherein said graft further comprises a second hem disposed at said proximal end of said prosthetic component and defining a second interior space and said device further comprises a second cord disposed within said second interior space.

5. The device of claim 3, wherein said cord is in a compressed state prior to being contacted with fluid.

6. The device of claim 5, wherein the thickness of said cord in the compressed state is less than thirty thousandths of an inch.

7. The device of claim 1, wherein said cord has a flat ribbon shape.

8. The device of claim 1, wherein said cord has a shape selected from the group consisting of annular, circular, semi-circular, D-shaped, rectangular, octagonal, trapezoidal, triangular, and square.

9. The device of claim 1 further comprising an outer coating formed over said cord, wherein said coating dissolves upon exposure to fluid for varying the rate at which said cord expands after deployment of said device.

10. The device of claim 1, wherein said hem has holes to adjust the porosity of said hem for allowing fluid to contact said cord.

11. The device of claim 1, wherein said hem is sufficiently ductile to conform to irregular shapes.

12. The device of claim 2, wherein said hem is positioned to allow said stent to protrude distally relative to said hem.

13. The device of claim 12, wherein at least one hoop of said stent is distal relative to said hem.

14. The device of claim 1, wherein said graft has a first permeability at areas remote from said hem and a second permeability, greater than said first permeability, at said hem.

15. The device of claim 1 further comprising an attachment tab having a first part attached to the graft and a second part extending radially outward of said first part for attachment to an adjacent area of the body surrounding the prosthetic component.

16. A method for implanting a device in a body lumen comprising the steps of:
    introducing a device into a body lumen, wherein said device comprises: a prosthetic component having a proximal end and a distal end and comprising a graft extending between said proximal end and said distal end and having a hem formed on said proximal end or said distal end, wherein said hem defines an interior space; and a cord disposed within said interior space for expanding upon absorbing fluid; and
    contacting said cord with fluid to aid in fixating said prosthetic component against said body lumen.

17. The method of claim 16, wherein introducing said device comprises the following steps:
    compressing the device into an introducer;
    inserting the introducer into the body lumen;
    positioning the introducer such that the compressed prosthetic component is at a predetermined location within the body lumen; and
    withdrawing the introducer to expand the prosthetic component to its decompressed size at the predetermined location within the body lumen.

18. The method of claim 16, wherein contacting said cord with fluid comprises the following steps:
    aligning the outside circumference of the hem within the inside diameter of the body lumen; and
    removing an impediment to the flow of fluid within the body lumen to said cord.

19. A device for implantation in a body lumen comprising:
    a prosthetic component comprising a graft having a hem formed on said graft, wherein said hem defines an interior space, and a stent disposed radially inside said graft; and
    a cord disposed within said interior space adapted for expanding upon absorbing fluid for aiding in fixating said prosthetic component against said body lumen.

20. A device for implantation in a body lumen comprising:
    a prosthetic component having a proximal end and a distal end and comprising a graft having a first hem formed on said graft at said distal end, wherein said hem defines a first interior space, and a second hem formed on said graft at said proximal end, wherein said second hem defines a second interior space;
    a first cord disposed within said first interior space adapted for expanding upon absorbing fluid for aiding in fixating said prosthetic component against said body lumen; and
    a second cord adapted for expanding upon absorbing fluid for aiding in fixating said prosthetic component against said body lumen disposed within said second interior space.

21. A device for implantation in a body lumen comprising:
    a prosthetic component having a distal end and comprising a graft having a hem formed on said graft at said distal end, wherein said hem defines an interior space; and
    a cord, disposed within said interior space adapted for expanding upon absorbing fluid for aiding in fixating said prosthetic component against said body lumen, wherein said cord is in a compressed state having a thickness less than thirty thousandths of an inch prior to being contacted with fluid.

22. A device for implantation in a body lumen comprising:
    a prosthetic component comprising a graft having a hem formed on said graft, wherein said hem defines an interior space and said hem is sufficiently ductile to conform to irregular shapes; and
    a cord disposed within said interior space adapted for expanding upon absorbing fluid for aiding in fixating said prosthetic component against said body lumen.

23. The device of claim 19, wherein said hem is positioned to allow said stent to protrude distally relative to said hem.

24. The device of claim 23, wherein at least one hoop of said stent is distal relative to said hem.

25. A device for implantation in a body lumen comprising:

a prosthetic component comprising a graft having a hem formed on said graft, wherein said graft has a first permeability at areas remote from said hem and a second permeability, greater than said first permeability, at said hem, and wherein said hem defines an interior space; and a cord disposed within said interior space adapted for expanding upon absorbing fluid for aiding in fixating said prosthetic component against said body lumen.

26. A method of implanting a device in a body lumen comprising the steps of:

compressing said device into an introducer wherein said device comprises: a prosthetic component comprising a graft having a hem formed on said graft, wherein said hem defines an interior space and a cord disposed within said interior space for expanding upon absorbing said fluid;

inserting said introducer into said body lumen;

positioning said introducer such that said compressed prosthetic component is at a predetermined location within said body lumen;

withdrawing said introducer to expand the prosthetic component to its decompressed size at said predetermined location within the body lumen; and contacting said cord with fluid to aid in fixating said prosthetic component against said body lumen.

27. A method of implanting a device in a body lumen comprising the steps of:

introducing said device into said body lumen wherein said device comprises: a prosthetic component comprising a graft having a hem formed on said graft, wherein said hem defines an interior space; and a cord disposed within said interior space for expanding upon absorbing said fluid to aid in fixating said prosthetic component against said body lumen;

aligning an outside circumference of the hem within an inside diameter of said body lumen; and removing an impediment to a flow of a fluid within said body lumen to said cord, to allow said fluid to contact said cord.

28. The device of claim 1, wherein said cord consists of an absorbent material which absorbs fluid and expands as a result of the absorption of fluid.

29. The method of claim 16, wherein said cord consists of an absorbent material which, upon the contacting step, absorbs fluid and expands as a result of the absorption of fluid.

30. The device of claim 19, wherein said cord consists of an absorbent material which absorbs fluid and expands as a result of the absorption of fluid.

31. The device of claim 20, wherein said first and second cord consist of an absorbent material which absorbs fluid and expands as a result of the absorption of fluid.

32. The device of claim 21, wherein said cord consists of an absorbent material which absorbs fluid and expands as a result of the absorption of fluid.

33. The device of claim 22, wherein said cord consists of an absorbent material which absorbs fluid and expands as a result of the absorption of fluid.

34. The device of claim 25, wherein said cord consists of an absorbent material which absorbs fluid and expands as a result of the absorption of fluid.

35. The method of claim 26, wherein said cord consists of an absorbent material which, upon the contacting step, absorbs fluid and expands as a result of the absorption of fluid.

36. The method of claim 27, wherein said cord consists of an absorbent material which, upon said fluid contacting said cord, absorbs fluid and expands as a result of the absorption of fluid.

* * * * *